United States Patent
Connelly et al.

(10) Patent No.: US 9,216,998 B2
(45) Date of Patent: Dec. 22, 2015

(54) TRICYCLIC INDOLE DERIVATIVES USEFUL ENDOTHELIAL LIPASE INHIBITORS

(71) Applicant: Janssen Pharmaceutica, NV, Beerse (BE)

(72) Inventors: Margery A. Connelly, Lansdale, PA (US); Michael Greco, Lansdale, PA (US); Hong Ye, Lansdale, PA (US)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 13/766,826

(22) Filed: Feb. 14, 2013

(65) Prior Publication Data

US 2013/0210806 A1   Aug. 15, 2013

Related U.S. Application Data

(60) Provisional application No. 61/599,066, filed on Feb. 15, 2012.

(51) Int. Cl.
| | |
|---|---|
| *C07D 471/06* | (2006.01) |
| *C07D 487/06* | (2006.01) |
| *C07D 498/06* | (2006.01) |
| *C07D 513/06* | (2006.01) |

(52) U.S. Cl.
CPC ............ *C07D 513/06* (2013.01); *C07D 471/06* (2013.01); *C07D 487/06* (2013.01); *C07D 498/06* (2013.01)

(58) Field of Classification Search
CPC .. C07D 513/06; C07D 487/06; C07D 498/06; C07D 471/06
See application file for complete search history.

(56) References Cited

U.S. PATENT DOCUMENTS

| | | | |
|---|---|---|---|
| 5,278,326 A | 1/1994 | Augelli-Szafran et al. | |
| 5,324,725 A | 6/1994 | Jasserand et al. | |
| 5,474,988 A * | 12/1995 | Demonchaux et al. | .... 514/224.5 |
| 2003/0087883 A1* | 5/2003 | Fu | ................... 514/151 |
| 2005/0107616 A1 | 5/2005 | Barrett et al. | |
| 2007/0088025 A1* | 4/2007 | Adam-Worrall | ........... 514/224.5 |

FOREIGN PATENT DOCUMENTS

| | | |
|---|---|---|
| EP | 0415 776 | 3/1991 |
| WO | 2004/076411 A2 | 9/2004 |
| WO | 2009/002807 A2 | 12/2008 |
| WO | 2009/112832 | 9/2009 |

OTHER PUBLICATIONS

Rodrigues, I., et al., "1-Trifluoromethyl Epoxy Ethers. Effect of Hexafluoro-2-propanol on Reactions with Secondary Aromatic Amines: Synthesis of 3-Trifluoromethyl Indole Derivatives", J. Org. Chem., 2001, pp. 2098-2103, vol. 66, Issue 6.
International Search Report—PCT/US2013/026257, Dated Apr. 22, 2013.
Ma, et al., "Endothelial Lipase is a Major Genetic Determinant for High-Density Lipoprotein Concentration, Structure, and Metabolism" Proceedings in the National Academy of Science, 2003, pp. 2748-2753, vol. 100.

* cited by examiner

*Primary Examiner* — James D Anderson
(74) *Attorney, Agent, or Firm* — Yuriy P. Stercho

(57) ABSTRACT

The present invention is directed to tricyclic indole derivatives, pharmaceutical compositions containing them and their use in the treatment of disorders and conditions modulated by endothelial lipase, for example, cardiovascular disorders.

16 Claims, No Drawings

TRICYCLIC INDOLE DERIVATIVES USEFUL ENDOTHELIAL LIPASE INHIBITORS

CROSS REFERENCE TO RELATED APPLICATIONS

The present application claims benefit of U.S. Provisional Patent Application Ser. No. 61/599,066, filed on Feb. 15, 2012, which is incorporated herein by reference in its entirety and for all purposes.

FIELD OF THE INVENTION

The present invention is directed to tricyclic indole derivatives, pharmaceutical compositions containing them and their use in the treatment of disorders and conditions modulated by endothelial lipase. More particularly, the compounds of the present invention are endothelial lipase inhibitors, useful in the treatment of cardiovascular disorder.

BACKGROUND OF THE INVENTION

Endothelial lipase (EL), a serine-phospholipase, is a member of the triglyceride lipase family first cloned in 1999. Unlike other triglyceride lipases, EL has a dramatic difference in substrate preference, possessing predominantly phospholipase activity rather than triglyceride lipase activity. Importantly, a role for EL in the regulation of HDL cholesterol in mice has been well-documented. EL knockout mice have a pronounced elevation in HDL cholesterol relative to wild type mice. Moreover, recent studies suggest that EL may have a pro-inflammatory effect and may be involved in atherogenesis. Taken together, this evidence suggests that an EL inhibitor could have benefit in the treatment of cardiovascular disease.

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors. Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis.

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol. Endothelial lipase (also known as EDL, EL, LIPG, endothelial-derived lipase, and endothelial cell-derived lipase) is synthesized in endothelial cells, a characteristic that distinguishes it from the other members of the family. At least 50% of the variation in HDL cholesterol levels is genetically determined.

The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects. Notably, the endothelial lipase-mediated binding and uptake of HDL particles and the selective uptake of HDL-derived cholesterol esters have been reported to be independent of its enzymatic lipolytic activity. Recombinant endothelial lipase protein has substantial phospholipase activity but has been reported to have less hydrolytic activity toward triglyceride lipids. However, endothelial lipase does exhibit triglyceride lipase activity ex vivo in addition to its HDL phospholipase activity, and endothelial lipase was found to hydrolyze HDL more efficiently than other lipoproteins. Over expression of the human endothelial lipase gene in the livers of mice markedly reduces plasma concentrations of HDL cholesterol and its major protein apolipoprotein A-I (apoA-I).

There remains a need for compounds that can inhibit lipase, more particularly endothelial lipase, for the treatment of, for example, cardiovascular disorders.

SUMMARY OF THE INVENTION

The present invention is directed to compounds of formula (I)

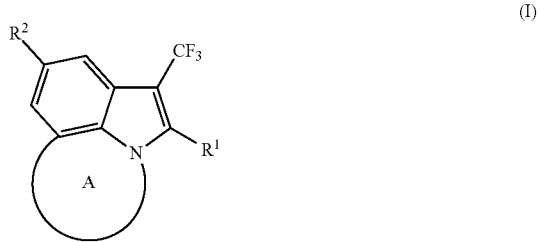

(I)

wherein $R^1$ is selected from the group consisting of —$(CH_2)_a$-phenyl and —$(CH_2)_b$—O-phenyl; wherein a is an integer from 1 to 5; b is an integer from 1 to 4; and wherein the phenyl portion of the $R^1$ group is optionally substituted with one to two substituents independently selected from the group consisting of halogen, $C_{1-4}$alkyl and $C_{1-4}$alkoxy;

$R^2$ is selected from the group consisting of hydrogen, hydroxy, methoxy and amino;

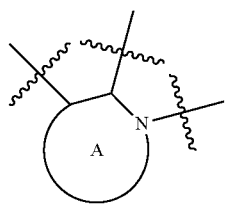

represents a five to seven membered, saturated ring structure selected from the group consisting of

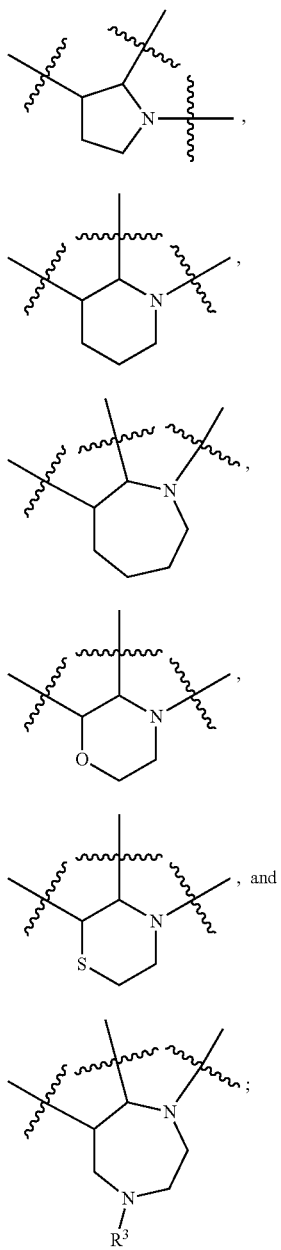

(a)

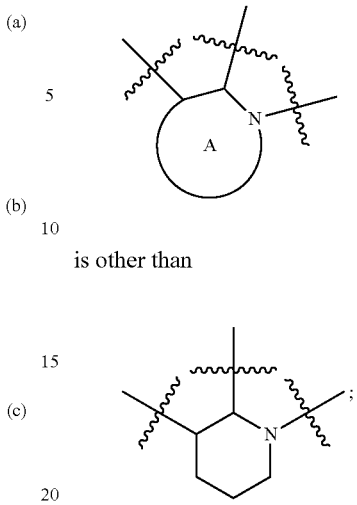

(b)

is other than (c)

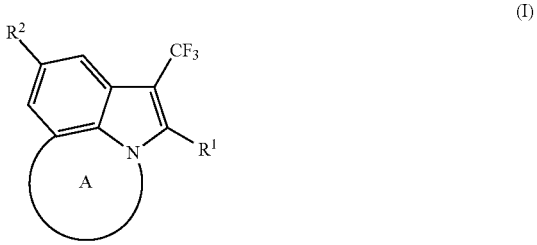

and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by endothelial lipase (selected from the group consisting of atherosclerosis, dyslipidemia, low HDL and high LDL) in a subject in need thereof comprising administering to the subject a therapeutically effective amount of any of the compounds or pharmaceutical compositions described above.

Another example of the invention is the use of any of the compounds described herein in the preparation of a medicament for treating: (a) atherosclerosis, (b) dyslipidemia, (c) low HDL or (d) high LDL, in a subject in need thereof.

DETAILED DESCRIPTION OF THE INVENTION

The present invention is directed to compounds of formula (I)

(I)

wherein $R^3$ is selected from the group consisting of hydrogen, —$C_{1-4}$alkyl, —($C_{1-4}$alkyl)-OH, —C(O)—($C_{1-4}$alkyl), —C(O)—($C_{1-3}$alkyl)-$CF_3$, —C(O)O—($C_{1-4}$alkyl), —C(O)—$CH_2$—O—C(O)—$C_{1-4}$alkyl), —C(O)—$NR^AR^B$, —C(O)—NH-phenyl, —C(O)—$CH_2$—$NR^AR^B$, —C(=NH)—$NR^AR^B$, —$SO_2$—($C_{1-4}$alkyl) and —$SO_2$—$NR^AR^B$; and wherein $R^A$ and $R^B$ are each independently selected from the group consisting of hydrogen and $C_{1-4}$alkyl;

provided that when $R^1$ is —$CH_2CH_2$-phenyl and $R^2$ is hydrogen, then wherein $R^1$, $R^2$ and

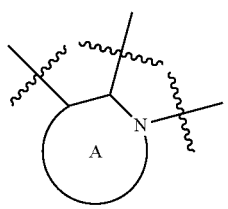

are as herein defined, and pharmaceutically acceptable salts thereof. The compounds of the present invention are endothelial lipase inhibitors, useful in the treatment of cardiovascular disorders including, but not limited to, atherosclerosis, dyslipidemia, low HDL, high LDL, and the like, preferably atherosclerosis or dyslipidemia. The compounds of formula (I) of the present invention were further found to be selective for inhibition of EL (endothelial lipase) over inhibition of LPL (lipoprotein lipase). The compounds of formula (I) of the present invention are therefore preferred over non-selective EL inhibitors, as inhibition of LPL can lead to the undesired effect of increased triglyceride levels.

In an embodiment of the present invention,

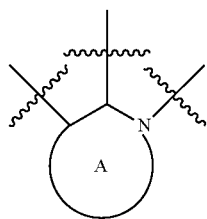

is selected from the group consisting of

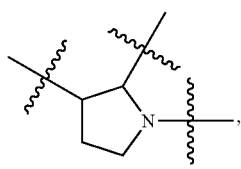

(a)

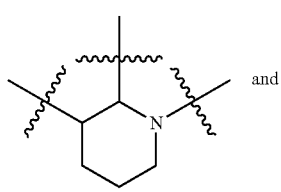

(b)

and

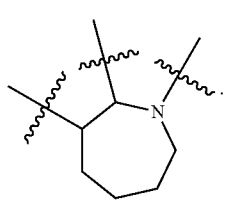

(c)

In another embodiment of the present invention,

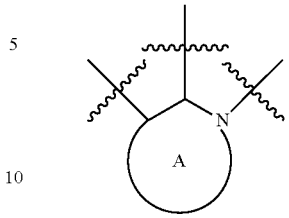

is selected from the group consisting of

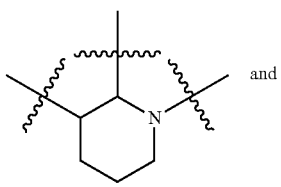

(b)

and

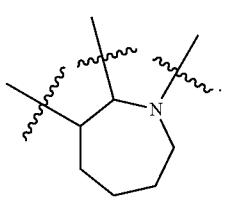

(c)

In another embodiment, the present invention is directed to compounds of formula (I) wherein

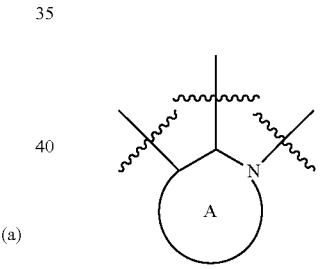

is selected from the group consisting of

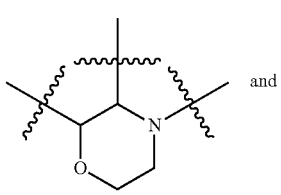

(d)

and

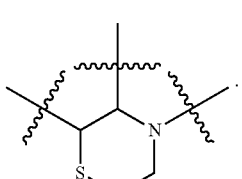

(e)

In additional embodiment, the present invention is directed to compounds of formula (I) wherein

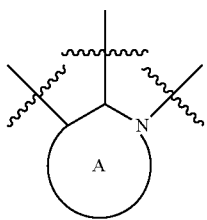

is one or more five to seven membered ring structures independently selected from (a), (b), (c), (d), (e) and (f), as herein defined.

In an embodiment, the present invention is directed to compounds of formula (Ia)

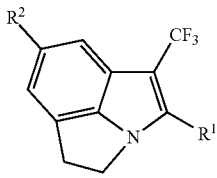

(Ia)

and pharmaceutically acceptable salts thereof, wherein $R^1$ and $R^2$ are as herein described. In another embodiment, the present invention is directed to compounds of formula (Ib)

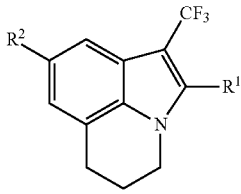

(Ib)

and pharmaceutically acceptable salts thereof, wherein $R^1$ and $R^2$ are as herein described. In another embodiment, the present invention is directed to compounds of formula (Ic)

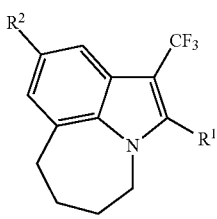

(Ic)

and pharmaceutically acceptable salts thereof, wherein $R^1$ and $R^2$ are as herein described. In another embodiment, the present invention is directed to compounds of formula (Id)

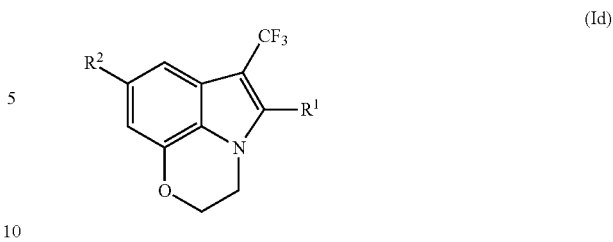

(Id)

and pharmaceutically acceptable salts thereof, wherein $R^1$ and $R^2$ are as herein described. In another embodiment, the present invention is directed to compounds of formula (Ie)

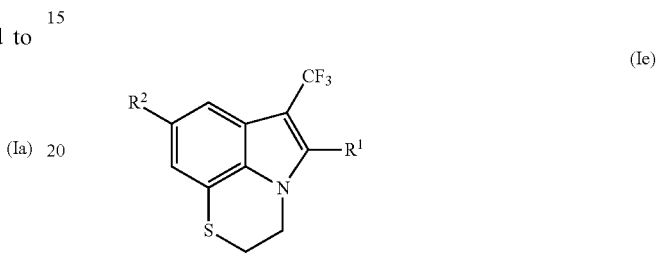

(Ie)

and pharmaceutically acceptable salts thereof, wherein $R^1$ and $R^2$ are as herein described. In another embodiment, the present invention is directed to compounds of formula (If)

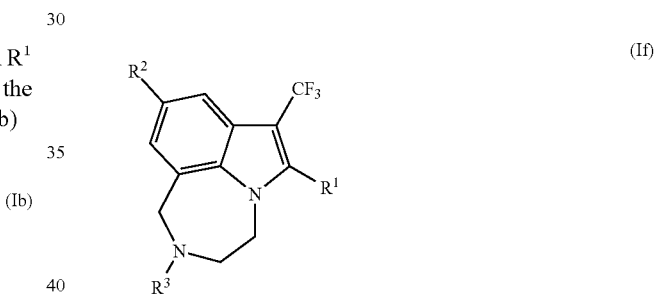

(If)

and pharmaceutically acceptable salts thereof, wherein $R^1$, $R^2$ and $R^3$ are as herein described.

In an embodiment, the present invention is directed to compounds of formula (I) wherein $R^1$ is selected from the group consisting of —($C_{1-4}$alkyl)-phenyl and —($C_{1-3}$alkyl)-O-phenyl; wherein the phenyl portion of $R^1$ is optionally substituted with one to two substituents independently selected form the group consisting of halogen, $C_{1-2}$alkyl and $C_{1-2}$alkoxy. In another embodiment, the present invention is directed to compounds of formula (I) wherein $R^1$ is selected from the group consisting of —($C_{1-3}$alkyl)-phenyl and —($C_{1-3}$alkyl)-O-phenyl.

In another embodiment, the present invention is directed to compounds of formula (I) wherein $R^1$ is selected from the group consisting of —$CH_2$-phenyl, —$CH_2CH_2$-phenyl, —$CH_2CH_2CH_2$-phenyl and —$CH_2CH_2CH_2$—O-phenyl. In another embodiment, the present invention is directed to compounds of formula (I) wherein $R^1$ is selected from the group consisting of —$CH_2$-phenyl, —$CH_2CH_2$-phenyl and —$CH_2CH_2CH_2$—O-phenyl. In another embodiment, the present invention is directed to compounds of formula (I) wherein $R^1$ is selected from the group consisting of —$CH_2CH_2$-phenyl, —$CH_2CH_2CH_2$-phenyl and —$CH_2CH_2CH_2$—O-phenyl. In another embodiment, the present invention is directed to compounds of formula (I)

wherein R¹ is selected from the group consisting of —CH₂-phenyl, —CH₂CH₂-phenyl and —CH₂CH₂CH₂-phenyl. In another embodiment, the present invention is directed to compounds of formula (I) wherein R¹ is —CH₂CH₂-phenyl. In another embodiment, the present invention is directed to compounds of formula (I) wherein R¹ is selected from the group consisting of —CH₂CH₂CH₂—O-phenyl.

In an embodiment, the present invention is directed to compounds of formula (I) wherein R² is selected from the group consisting of hydroxy, methoxy and amino. In another embodiment, the present invention is directed to compounds of formula (I) wherein R² is selected from the group consisting of methoxy and amino. In another embodiment, the present invention is directed to compounds of formula (I) wherein R² is hydrogen. In another embodiment, the present invention is directed to compounds of formula (I) wherein R² is amino.

In an embodiment, the present invention is directed to compounds of formula (I) wherein R³ is selected from the group consisting of hydrogen, —(C$_{1-2}$alkyl), —(C$_{1-4}$alkyl)-OH, —C(O)—(C$_{1-2}$alkyl), —C(O)—(C$_{1-3}$alkyl)-CF₃, —C(O)O—(C$_{1-4}$alkyl), —C(O)—CH₂—O—C(O)—(C$_{1-4}$alkyl), —C(O)—NR$^A$R$^B$, —C(O)—NH-phenyl, —C(O)—CH₂—NR$^A$R$^B$, —C(=NH)—NH₂, —SO₂—(C$_{1-4}$alkyl) and —SO₂—NR$^A$R$^B$; and wherein R$^A$ and R$^B$ are each independently selected from the group consisting of hydrogen and C$_{1-4}$alkyl. In another embodiment, the present invention is directed to compounds of formula (I) wherein R³ is selected from the group consisting of hydrogen, —(C$_{1-2}$alkyl)-OH, —C(O)—(C$_{1-3}$alkyl)-CF₃, —C(O)O—(C$_{1-4}$alkyl), —C(O)—CH₂—O—C(O)—(C$_{1-2}$alkyl), —C(O)—NHR$^A$, —C(O)—NH-phenyl, —C(O)—CH₂—NR$^A$R$^B$, —C(=NH)—NH₂, —SO₂—(C$_{1-2}$alkyl) and —SO₂—NH₂; and wherein R$^A$ and R$^B$ are each independently selected from the group consisting of hydrogen and C$_{1-4}$alkyl.

In another embodiment, the present invention is directed to compounds of formula (I) wherein R³ is selected from the group consisting of hydrogen, —CH₂CH₂—OH, —C(O)—O—C(CH₃)₃, —C(O)—CH₂—CF₃, —C(O)—CH₂—CH(CH₃)—CF₃, —C(O)—CH₂—O—C(O)—CH₃, —C(O)—NH—CH(CH₃)₂, —C(O)—NH-phenyl, —C(O)—CH₂—NH₂, —C(O)—CH₂—N(CH₃)₂, —C(=N)—NH₂, —SO₂—CH₃ and —SO₂—NH₂. In another embodiment, the present invention is directed to compounds of formula (I) wherein R³ is selected from the group consisting of —C(O)—O—C(CH₃)₃, —C(O)—CH₂—CH(CH₃)—CF₃, —C(O)—NH—CH(CH₃)₂, —C(O)—NH-phenyl, —SO₂—CH₃ and —SO₂—NH₂. In another embodiment, the present invention is directed to compounds of formula (I) wherein R³ is selected from the group consisting of —C(O)—CH₂—CH(CH₃)—CF₃, —C(O)—NH—CH(CH₃)₂ and —SO₂—NH₂.

In an embodiment, the present invention is directed to compounds of formula (I) wherein when R¹ is —CH₂CH₂-phenyl and R² is hydrogen, then

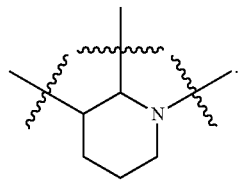 [SMILES: *C1CCCN(*)C1*]

is other than

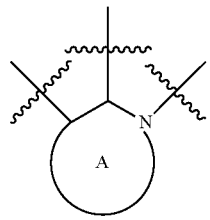

In an embodiment, the present invention is directed to compounds of formula (I) wherein

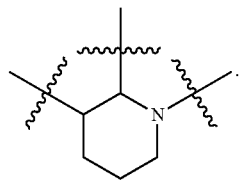

is other than

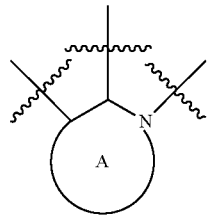

In another embodiment, the present invention is directed to compounds of formula (I) wherein

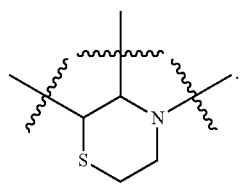

is other than

Additional embodiments of the present invention, include those wherein the substituents selected for one or more of the variables defined herein (e.g. R¹, R², R³, R$^A$, R$^B$ and/or are independently selected to be any individual substituent or any subset of substituents selected from the complete list as defined herein. In another embodiment, the present invention is directed to any single compound or subset of compounds selected from the representative compounds listed in Tables 1-3, below.

Representative compounds of the present invention are as listed in Tables 1-3, below.

TABLE 1

Representative Compounds of Formula (I)

| Compound No. | R¹ | R² |
|---|---|---|
| 1 | —(CH₂CH₂CH₂)-phenyl | H |
| 3 | —(CH₂)-phenyl | H |
| 4 | —(CH₂CH₂CH₂)-phenyl | H |

TABLE 1-continued

Representative Compounds of Formula (I)

| Compound No. | R¹ | R² |
|---|---|---|
| 5 | —(CH₂CH₂)-phenyl | —OCH₃ |
| 6 | —(CH₂CH₂)-phenyl | —OH |
| 7 | —(CH₂CH₂)-phenyl | H |
| 8 | —(CH₂CH₂CH₂)—O-phenyl | —NH₂ |
| 9 | —(CH₂CH₂)-phenyl | H |

TABLE 1-continued

Representative Compounds of Formula (I)

[Structure: indole fused with ring A, with R² at position, CF₃, R¹, N]

[Structure showing ring A attached to N]

| Compound No. | R¹ | R² |
|---|---|---|
| 10 | —(CH₂)-phenyl | H |

[Structure: 7-membered N-containing ring]

| 11 | —(CH₂CH₂CH₂)-phenyl | H |

[Structure: 7-membered N-containing ring]

TABLE 2

Representative Compounds of Formula (I)

[Structure: indole fused system with R², CF₃, R¹, and N—R³ containing ring]

| Compound No. | R¹ | R² | R³ |
|---|---|---|---|
| 12 | —(CH₂CH₂)-phenyl | H | —C(O)—NH—CH(CH₃)₂ |
| 13 | —(CH₂CH₂)-phenyl | H | —C(O)—O—C(CH₃)₃ |
| 14 | —(CH₂CH₂)-phenyl | H | —C(O)—NH-phenyl |
| 15 | —(CH₂CH₂)-phenyl | H | H |
| 16 | —(CH₂CH₂)-phenyl | H | —C(O)—CH₂—N(CH₃)₂ |
| 17 | —(CH₂CH₂)-phenyl | H | C(=N)—NH₂ |
| 18 | —(CH₂CH₂)-phenyl | H | —C(O)—CH₂—NH₂ |

TABLE 2-continued

Representative Compounds of Formula (I)

[Structure: same as above]

| Compound No. | R¹ | R² | R³ |
|---|---|---|---|
| 19 | —(CH₂CH₂)-phenyl | H | —SO₂—NH₂ |
| 20 | —(CH₂CH₂)-phenyl | H | —C(O)—CH₂—O—C(O)—CH₃ |
| 21 | —(CH₂CH₂)-phenyl | H | —C(O)—CH₂—CF₃ |
| 22 | —(CH₂CH₂)-phenyl | H | —C(O)—CH₂—CH(CH₃)—CF₃ |
| 23 | —(CH₂CH₂)-phenyl | H | —CH₂CH₂—OH |
| 24 | —(CH₂CH₂)-phenyl | H | —SO₂—CH₃ |

TABLE 3

Representative Compounds of Formula (I)

[Structure: indole fused with ring A, R², CF₃, R¹]

[Structure showing ring A attached to N]

| Compound No. | R¹ | R² |
|---|---|---|
| 25 | —(CH₂CH₂)-phenyl | H |

[Structure: morpholine ring]

| 26 | —(CH₂CH₂CH₂)-phenyl | H |

[Structure: morpholine ring]

TABLE 3-continued

Representative Compounds of Formula (I)

| Compound No. | | $R^1$ | $R^2$ |
|---|---|---|---|
| 27 | 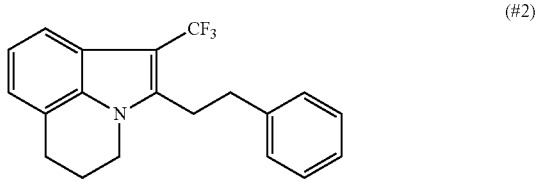 | —(CH$_2$CH$_2$CH$_2$)—O-phenyl | H |
| 28 | | —(CH$_2$CH$_2$CH$_2$)-phenyl | H |

The following reference compound

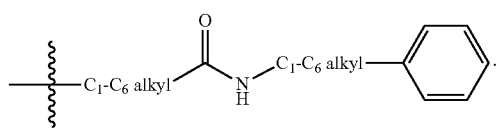

(#2)

also known as 2-phenethyl-1-(trifluoromethyl)-5,6-dihydro-4H-pyrrolo[3,2,1-ij]quinoline (CA Registry number 866049-84-5, Registered Oct. 25, 2005) is commercially available from multiple sources including, for example, Key Organics, Ltd. (Highfield Road Industrial Estate, Camelford, Cornwall, PL32 9RA, United Kingdom).

As used herein, "halogen" shall mean chlorine, bromine, fluorine and iodine, preferably chlorine or fluorine, more preferably fluorine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{1-4}$" when used with alkyl means a carbon chain composition of 1-4 carbon atoms.

One skilled in the art will recognize that the term "—(C$_{X-Y}$alkyl)-", wherein X and Y are integers, shall denote any C$_{X-Y}$alkyl carbon chain as herein defined, wherein said C$_{X-Y}$alkyl chain is divalent and is further bound through two points of attachment, preferably through two terminal carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{1-4}$" when used with alkoxy means an oxygen ether radical of the above described carbon chain alkyl group of 1-4 carbon atoms.

When a particular group is "substituted", said group may have one or more substituents, preferably from one to five substituents, more preferably from one to three substituents, most preferably from one to two substituents, independently selected from the list of substituents. With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula Abbreviations used in the specification, particularly the Schemes and Examples, are as follows:

| | |
|---|---|
| apoA-1 = | Apolipoprotein A-I |
| BOC or Boc or = t-Boc or tert-Boc | tert-Butoxycarbonyl (i.e. —C(O)—O—C(CH$_3$)$_3$) |
| CBz = | Carboxybenzyl (i.e. —C(O)O—CH$_2$-phenyl) |
| CETP = | Cholesteryl Ester Transfer Protein |
| DCM = | Dichloromethane |
| DIPEA or DIEA = | Diisopropylethylamine |
| DMF = | N,N-Dimethylformamide |
| DMSO = | Dimethylsulfoxide |
| EL or EDL or LIPG = | Endothelial Lipase |
| HATU = | O-(7-Azabenzotriazol-1-yl)-N,N,N",N"-Tetramethyl Uronium Hexafluorophosphate |
| HDL = | High Density Lipoprotein |
| HEPES = | 4-(2-Hydroxyethyl)-1-Piperizine Ethane Sulfonic Acid |
| HL = | Hepatic Lipase |
| HPLC = | High Performance Liquid Chromatography |
| LDL = | Low Density Lipoprotein |
| LPL = | Lipoprotein Lipase |
| mCPBA = | meta-Chloroperoxybenzoic Acid |
| Mesyl = | Methylsulfonyl |
| TEA = | Triethylamine |
| TFA = | Trifluoroacetic acid |
| TG = | Triglycerides |
| THF = | Tetrahydrofuran |
| Tosyl = | p-Toluenesulfonyl |
| VLDL = | Very Low Density Lipoprotein |

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, Protective Groups in Organic Synthesis, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α−obs]/[α−max])×100.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, a-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthetic Methods

Compounds of formula (I) wherein

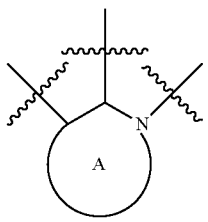

is selected from the group consisting of

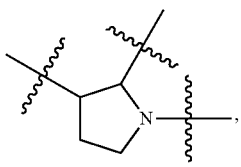

(a)

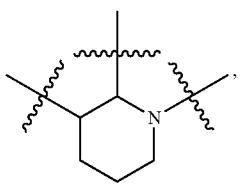 [SMILES: *C1CCCN(*)C1*]

(b)

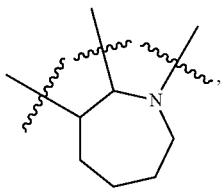

(c)

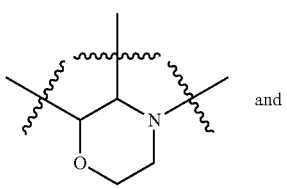

and (d)

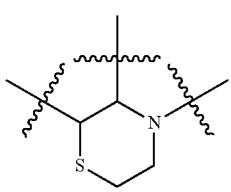

(e)

may be prepared according to the process outlined in Scheme 1.

Scheme 1

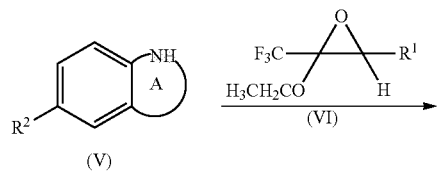

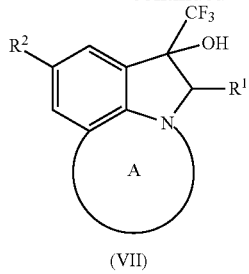

(VII)

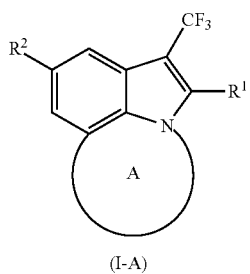

(I-A)

Accordingly, a suitably substituted compound of formula (V), a known compound or compound prepared by known methods, is reacted with a suitably substituted compound of formula (VI), a known compound or compound prepared by known methods, in an organic solvent such as 1,1,1,3,3,3-hexafluoropropan-2-ol, to yield the corresponding compound of formula (VII).

The compound of formula (VII) is reacted with a suitable selected dehydrating agent such as $SO_2Cl$, $POCl_3$, and the like, in the presence of a suitably selected organic base such as pyridine, DIPEA, TEA, and the like, neat or in a suitably selected organic solvent, at a temperature in the range of from about 0° C. to about room temperature, preferably, at a temperature of about 0° C.; to yield the corresponding compound of formula (I-A).

Compounds of formula (I) wherein

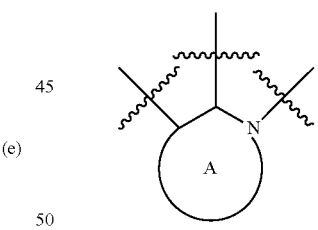

is

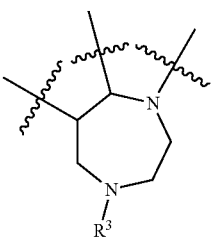

may be prepared according to the process outlined in Scheme 2.

Scheme 2

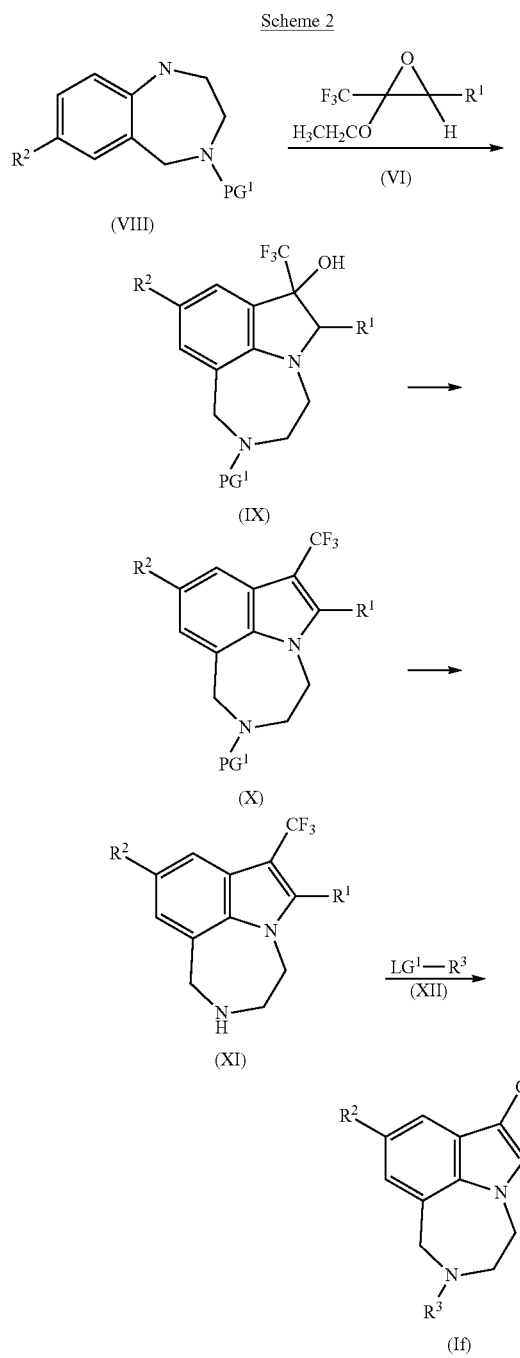

Accordingly, a suitably substituted compound of formula (VIII), wherein PG¹ is a suitably selected nitrogen protecting group such as BOC, CBz, and the like, preferably BOC, a known compound or compound prepared by known methods, is reacted with a suitably substituted compound of formula (VI), a known compound or compound prepared by known methods, in an organic solvent such as 1,1,1,3,3,3-hexafluoropropan-2-ol, to yield the corresponding compound of formula (IX).

The compound of formula (IX) is reacted with a suitable selected dehydrating agent such as $SO_2Cl$, $POCl_3$, and the like, in the presence of a suitably selected organic base such as pyridine, DIPEA, TEA, and the like, neat or in a suitably selected organic solvent, at a temperature in the range of from about 0° C. to about room temperature, preferably at a temperature of about 0° C.; to yield the corresponding compound of formula (X).

The compound of formula (X) is de-protected according to known methods, to yield the corresponding compound of formula (XI). For example, wherein PG¹ is BOC, the compound of formula (X) is de-protected by reacting with a suitably selected acid such as HCl, in a suitably selected organic solvent, such as 1,4-dioxane.

The compound of formula (XI) is reacted with a suitably substituted compound of formula (XII), wherein $LG^1$ is a suitably selected leaving groups such as Cl, Br, carboxylate, and the like, a known compound or compound prepared by known methods; according to known coupling and alkylation methods (to functionalize the de-protected nitrogen atom); to yield the corresponding compound of formula (If).

Compounds of formula (VI) are known compounds or compounds which may be prepared according to known methods, for example according to the process(es) as disclosed in RODRIGUES, I., et al., "1-Trifluoromethyl Epoxy Ethers. Effect of Hexafluoro-2-propanol on Reactions with Secondary Aromatic Amines: Synthesis of 3-Trifluoromethyl Indole Derivatives", *J. Org. Chem.*, 2001, pp 2098-2103, Vol. 66, Issue 6. In an example, compounds of formula (VI) may be prepared, for example, according to the process outlined in Scheme 3.

Scheme 3

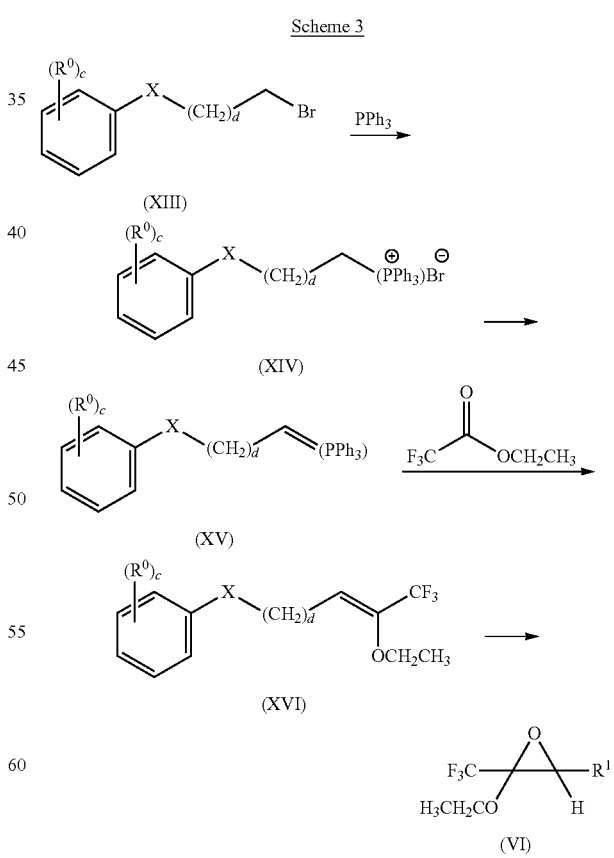

Accordingly, a suitably substituted compound of formula (XIII) wherein

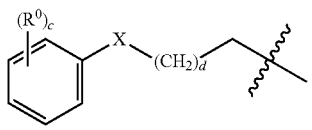

represents R¹, a known compound or compound prepared by known methods, is reacted triphenylphosphine, a known compound, in the presence of a suitably selected alkylating agent such as 2-bromoethylbenzene, 3-bromopropylbenzene, 4-bromobutylbenzene, 3-bromobutoxybenzene, 4-bromobutoxybenzene, and the like, in a suitably selected organic solvent such as toluene, benzene, and the like; to yield the corresponding compound of formula (XIV).

The compound of formula (XIV) is reacted with a suitably selected base such as NaH, KH, n-butyl lithium, NaNH$_2$, and the like, in a suitably selected organic solvent such as THF, toluene, benzene, and the like; at about reflux temperature; to yield the corresponding compound of formula (XV).

The compound of formula (XV) is reacted with ethyl 2,2,2-trifluoroacetate, a known compound; in a suitably selected organic solvent such as THF, toluene, and the like; at about reflux temperature; to yield the corresponding compound of formula (XVI).

The compound of formula (XVI) is reacted with a suitably selected oxidizing agent such as mCPBA, and the like, in a suitably selected organic solvent such as DCM, and the like; to yield the corresponding compound of formula (VI).

One skilled in the art will recognize that in Scheme 3 above, when R¹ is optionally substituted —(C$_{1-5}$alkyl)-phenyl, then in the compound of formula (XIII), X is absent, d is an integer from 0 to 4, c is an integer from 0 to 2 and each R⁰ is independently selected from the group consisting of halogen, C$_{1-4}$alkyl and C$_{1-4}$alkoxy. Similarly, in Scheme 3 above, when R¹ is optionally substituted —(C$_{1-4}$alkyl)-O-phenyl, then in the compound of formula (XIII), X is —O—, d is an integer from 0 to 3, c is an integer from 0 to 2 and each R⁰ is independently selected from the group consisting of halogen, C$_{1-4}$alkyl and C$_{1-4}$alkoxy.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1000 mg or any amount range therein, and may be given at a dosage of from about 0.01 to about 15 mg/kg/day, or any amount range therein, preferably from about 0.1 to about 10 mg/kg/day, or any amount range therein, preferably from about 0.5 to about 5 mg/kg/day, or any amount range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably, between about 1.0 mg and about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

The daily dosage of the products may be varied over a wide range from about 0.01 to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 15 mg/kg of body weight per day, or any amount or range therein. Preferably, the range is from about 0.1 to about 10.0 mg/kg of body weight per day, or any amount or range therein. More preferably, from about 0.5 to about 5.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Synthesis Example 1

Compound #9

2-phenethyl-1-(trifluoromethyl)-4,5,6,7-tetrahydroazepino[3,2,1-hi]indole

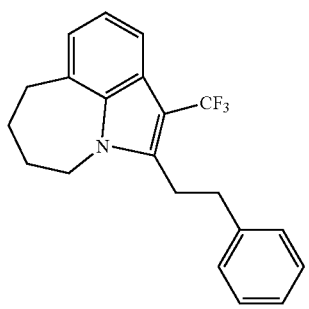 [SMILES: FC(F)(F)c1c(CCc2ccccc2)n2c3c(cccc13)CCCC2]

A solution of 2-ethoxy-3-phenethyl-2-(trifluoromethyl) oxirane (300 mg, 1.15 mmol; prepared as described in RODRIGUES, I., et al., "1-Trifluoromethyl Epoxy Ethers. Effect of Hexafluoro-2-propanol on Reactions with Secondary Aromatic Amines: Synthesis of 3-Trifluoromethyl Indole Derivatives", J. Org. Chem., 2001, pp 2098-2103, Vol. 66, Issue 6) and 2,3,4,5-tetrahydro-1H-benzo[b]azepine (170 mg, 1.15 mmol) in hexafluoroisopropanol was stirred at room temperature for 48 h. The solvent was evaporated to yield 2-phenethyl-1-(trifluoromethyl)-1,2,4,5,6,7-hexahydroazepino[3,2,1-hi]indol-1-ol (150 mg, 36%) as a diastereomeric mixture, that was used in the next step without further purification.

To a solution of 2-phenethyl-1-(trifluoromethyl)-1,2,4,5,6,7-hexahydroazepino[3,2,1-hi]indol-1-ol (50 mg, 0.14 mmol) in pyridine (3 mL) was added thionyl chloride (16 mg, 0.14 mmol) at 0° C. After stirring for 2 h at 0° C., the solvent was evaporated and the residue acidified with 1 N HCl. The resulting mixture was extracted with diethyl ether, and the organic phase was washed with brine, dried and concentrated. The resulting residue was purified by silica gel chromatography to yield 2-phenethyl-1-(trifluoromethyl)-4,5,6,7-tetrahydroazepino[3,2,1-hi]indole (8 mg).

$^1$H NMR (400 MHz, CDCl$_3$) δ 2.00-2.10 (m, 4H), 2.89-2.93 (m, 2H), 3.10-3.18 (m, 4H), 4.07 (2H, t, J=5 Hz), 6.91-7.32 (m, 7H), 7.55 (d, 1H, J=8 Hz); MS m/z 344 (MH)$^+$

Compounds 1, 3-8, and 9-11 were similarly prepared according to procedure as described in Example 1, using the selecting and reacting the appropriate oxirane intermediate (i.e. 2-ethoxy-3-phenethyl-2-(trifluoromethyl)oxirane; 3-benzyl-2-ethoxy-2-(trifluoromethyl)oxirane; 2-ethoxy-3-(3-phenylpropyl)-2-(trifluoromethyl)oxirane; or 2-ethoxy-3-(3-phenoxypropyl)-2-(trifluoromethyl)oxirane) with a commercially available amine.

3-Benzyl-2-ethoxy-2-(trifluoromethyl)oxirane and 2-ethoxy-3-(3-phenylpropyl)-2-(trifluoromethyl)oxirane were prepared by reacting benzyl bromide and phenylpropyl bromide, respectively, according to the methods described in RODRIGUES, I., et al., "1-Trifluoromethyl Epoxy Ethers. Effect of Hexafluoro-2-propanol on Reactions with Secondary Aromatic Amines: Synthesis of 3-Trifluoromethyl Indole Derivatives", J. Org. Chem., 2001, pp 2098-2103, Vol. 66, Issue 6. 2-Ethoxy-3-(3-phenoxypropyl)-2-(trifluoromethyl) oxirane was similarly prepared by reacting 4-phenoxybutyl bromide, according to the methods as described in RODRIGUES, I., et al., "1-Trifluoromethyl Epoxy Ethers. Effect of Hexafluoro-2-propanol on Reactions with Secondary Aromatic Amines: Synthesis of 3-Trifluoromethyl Indole Derivatives", J. Org. Chem., 2001, pp 2098-2103, Vol. 66, Issue 6.

| Compound No. | Measured MH$^+$ |
| --- | --- |
| 1 | 330 |
| 3 | 316 |
| 4 | 344 |
| 5 | 360 |
| 6 | 346 |
| 7 | 360 |
| 8 | 345 |
| 9 | 344 |
| 10 | 344 |
| 11 | 358 |

Synthesis Example 2

Compound #15

6-phenethyl-7-(trifluoromethyl)-1,2,3,4-tetrahydro-[1,4]diazepino[6,7,1-hi]indole

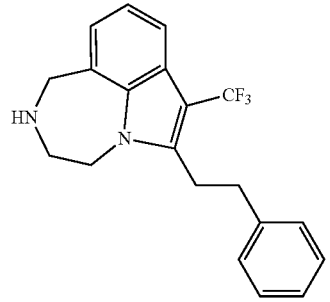 [SMILES: FC(F)(F)c1c(CCc2ccccc2)n2c3c(cccc13)CNCC2]

A solution of 2-ethoxy-3-phenethyl-2-(trifluoromethyl) oxirane (10 mmol) and tert-butyl 2,3-dihydro-1H-benzo[e][1,4]diazepine-4(5H)-carboxylate (10 mmol) in hexafluoroisopropanol (5 mL) was stirred at room temperature overnight, then heated at 53° C. until the reaction was complete. Solvent was evaporated and the residue was purified by reverse phase chromatography on a Gilson HPLC with a Kromasil column (10 u, 100 Å C18, column length 250×50 mm, gradient 42%→90% TFA-H$_2$O:acetonitrile) to yield tert-butyl 7-hydroxy-6-phenethyl-7-(trifluoromethyl)-3,4,6,7-tetrahydro-[1,4]diazepino[6,7,1-hi]indole-2(1H)-carboxylate (2.7 g, 58%).

Thionyl chloride (0.7 g; 5.8 mmol) was added to a solution of tert-butyl 7-hydroxy-6-phenethyl-7-(trifluoromethyl)-3,4,6,7-tetrahydro[1,4]diazepino[6,7,1-hi]indole-2(1H)-carboxylate (2.7 g; 5.8 mmol) in pyridine (7 mL) at O° C. After 2 h at 0° C., the resulting mixture was concentrated and the residue purified by silica gel chromatography (heptane-ethyl acetate) to yield tert-butyl 6-phenethyl-7-(trifluoromethyl)-3,4-dihydro-[1,4]diazepino[6,7,1-hi]indole-2(1H)-carboxylate (1.4 g, 53%).

To a solution of tert-butyl 6-phenethyl-7-(trifluoromethyl)-3,4-dihydro-[1,4]diazepino[6,7,1-hi]indole-2(1H)-carboxylate (1.4 g; 3.1 mmol) in CH$_2$Cl$_2$ at 0° C. was added 4M HCl in 1,4-dioxane (3.8 mL, 15.4 mmol). The resulting solution was warmed to room temperature and stirred overnight. The solid was collected to yield 6-phenethyl-7-(trifluoromethyl)-1,2,3,4-tetrahydro-[1,4]diazepino[6,7,1-hi]indole (1.1 g).

¹H NMR (400 MHz, CD₄OD) δ 2.98 (t, 2H, J=7 Hz), 3.29-3.31 (overlapping m, 2H), 3.42-3.47 (m, 2H), 4.38-4.40 (m, 2H), 4.70 (s, 2H), 7.14-7.55 (m, 7H), 7.66 (d, 1H, J=7 Hz); MS: m/z=345 (MH⁺)

Synthesis Example 3

Compound #19

6-phenethyl-7-(trifluoromethyl)-3,4-dihydro-[1,4]diazepino[6,7,1-hi]indole-2(1H)-sulfonamide

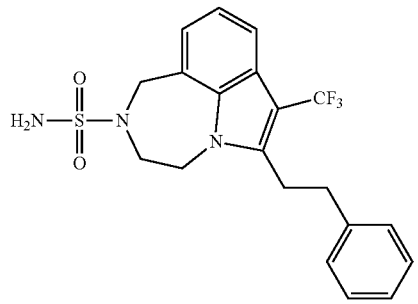 [SMILES: NS(=O)(=O)N1CCn2c(CCc3ccccc3)c(C(F)(F)F)c3cccc(c32)C1]

To a solution of 6-phenethyl-7-(trifluoromethyl)-1,2,3,4-tetrahydro-[1,4]diazepino[6,7,1-hi]indole (93 mg, 0.24 mmol) in dichloromethane (3 mL) was added diethylaminoethyl amine (0.13 mL, 0.73 mmol) and sulfamoyl chloride (42 mg, 0.37 mmol). After stirring overnight, another portion of sulfamoyl chloride (42 mg) was added at 0° C., and the resulting mixture stirred for 2 h at room temperature. The resulting mixture was then concentrated under reduced pressure, and the residue was purified by reverse-phase chromatography (gradient 42%→90% TFA-H₂O:acetonitrile) to yield 6-phenethyl-7-(trifluoromethyl)-3,4-dihydro-[1,4]diazepino[6,7,1-hi]indole-2(1H)-sulfonamide (32 mg).

¹H NMR (400 MHz, CD₃OD) δ 2.84 (t, 3H, J=7 Hz), 3.20-3.21 (m, 2H), 3.49-3.65 (m, 2H), 4.10-4.13 (m, 2H), 4.64 (s, 2H), 6.92-7.18 (m, 7H), 7.43 (d. 1H, J=8 Hz); MS m/z=345 (MH⁺)

Synthesis Example 4

Compound #12

N-isopropyl-6-phenethyl-7-(trifluoromethyl)-3,4-dihydro-[1,4]diazepino[6,7,1-hi]indole-2(1H)-carboxamide

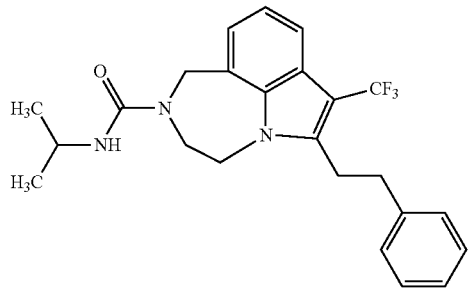 [SMILES: CC(C)NC(=O)N1CCn2c(CCc3ccccc3)c(C(F)(F)F)c3cccc(c32)C1]

The Boc group was removed from tert-butyl 7-hydroxy-6-phenethyl-7-(trifluoromethyl)-3,4,6,7-tetrahydro-[1,4]diazepino[6,7,1-hi]indole-2(1H)-carboxylate (138 mg, 0.3 mmol) (prepared as in Example 2 above) under standard conditions (CH₂Cl₂/trifluoroacetic acid) yielded 6-phenethyl-7-(trifluoromethyl)-1,2,3,4,6,7-hexahydro-[1,4]diazepino[6,7,1-hi]indol-6-ol trifluoroacetate, which was dissolved in THF (5 mL) and the resulting mixture was cooled to 0° C. Triethylamine (3.75 eq) was added, followed by addition of isopropyl isocyanate (1.7 eq). The resulting mixture was stirred at 0° C. for 30 min, then warmed to room temperature and stirred overnight. The resulting mixture was concentrated, dissolved in ethyl acetate (20 mL), and washed sequentially with water, NaHCO₃ (sat. aq.) and brine, then dried (Na₂SO₄) and concentrated to yield 7-hydroxy-N-isopropyl-6-phenethyl-7-(trifluoromethyl)-3,4,6,7-tetrahydro-[1,4]diazepino[6,7,1-hi]indole-2(1H)-carboxamide (134 mg, MH+=448).

The 7-hydroxy-N-isopropyl-6-phenethyl-7-(trifluoromethyl)-3,4,6,7-tetrahydro-[1,4]diazepino[6,7,1-hi]indole-2(1H)-carboxamide (9 mg, 0.021 mmol) was further processed with SOCl₂ and pyridine as described in Example 1, above to yield N-isopropyl-6-phenethyl-7-(trifluoromethyl)-3,4-dihydro-[1,4]diazepino[6,7,1-hi]indole-2(1H)-carboxamide (8 mg).

¹H NMR (400 MHz, CDCl₃) δ 2.93-2.96 (m, 2H), 3.17-3.20 (m, 2H), 3.68-3.75 (m, 2H), 3.82-3.90 (m, 1H), 4.09-4.15 (overlapping m, 3H), 5.30 (s, 2H), 7.03-7.32 (m, 7H), 7.64 (d, 8 Hz); MS m/z 430 (MH⁺)

Synthesis Example 5

Compound #13 tert-butyl 6-phenethyl-7-(trifluoromethyl)-3,4-dihydro-[1,4]diazepino[6,7,1-hi]indole-2(1H)-carboxylate

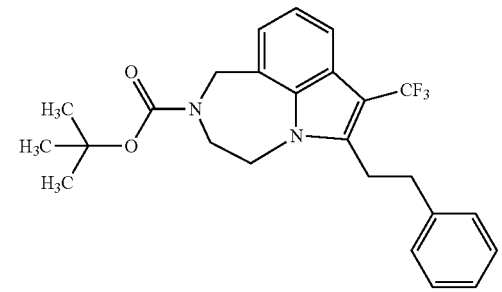 [SMILES: CC(C)(C)OC(=O)N1CCn2c(CCc3ccccc3)c(C(F)(F)F)c3cccc(c32)C1]

The title compound was similarly prepared as described in Example 2.

¹H NMR (400 MHz, CDCl₃) δ 1.40 (⅔ of s, 9H), 1.44 (⅓ of s, 9H), 2.91-2.96 (m, 2H), 3.16-3.20 (m, 2H), 4.81 (⅓ of s, 2H), 4.90 (⅔ of s, 2H), 6.99-7.36 (m, 7H), 7.63 (d, 1H, J=8 Hz); MS m/z 445 (MH⁺)

Synthesis Example 6

Compound #14

6-phenethyl-N-phenyl-7-(trifluoromethyl)-3,4-dihydro-[1,4]diazepino[6,7,1-hi]indole-2(1H)-carboxamide

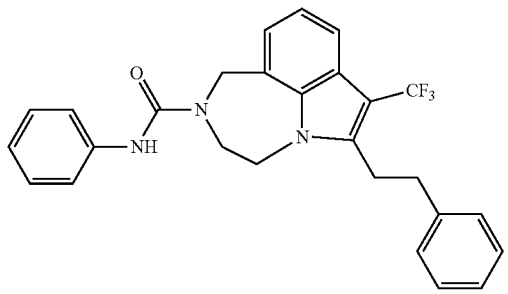 [SMILES: O=C(Nc1ccccc1)N1CCn2c(CCc3ccccc3)c(C(F)(F)F)c3cccc(c32)C1]

Phenyl isocyanate (3.8 mg, 0.05 mmol) was added to a solution of 6-phenethyl-7-(trifluoromethyl)-1,2,3,4,6,7-hexahydro-[1,4]diazepino[6,7,1-hi]indol-6-ol trifluoroacetate (14 mg, 0.039 mmol) in THF (3 mL) containing triethylamine (11 mg, 0.11 mmol) at 0° C. The resulting mixture was stirred at 0° C. for 30 min, then stirred at room temperature overnight. The resulting mixture was concentrated under reduced pressure, the residue dissolved in ethyl acetate and the resulting solution was washed sequentially with water, NaHCO$_3$ (sat'd. aq) and brine. The organic phase was dried (Na$_2$SO$_4$) and concentrated to yield 6-hydroxy-6-phenethyl-N-phenyl-7-(trifluoromethyl)-3,4,6,7-tetrahydro-[1,4]diazepino[6,7,1-hi]indole-2(1H)-carboxamide (MH+=482).

The 6-hydroxy-6-phenethyl-N-phenyl-7-(trifluoromethyl)-3,4,6,7-tetrahydro-[1,4]diazepino[6,7,1-hi]indole-2(1H)-carboxamide was further processed with thionyl chloride and pyridine as described in Example 1, above to yield 6-phenethyl-N-phenyl-7-(trifluoromethyl)-3,4-dihydro-[1,4]diazepino[6,7,1-hi]indole-2(1H)-carboxamide (5 mg).

$^1$H NMR (400 MHz, CDCl$_3$) δ 2.93-2.97 (m, 2H), 3.17-3.21 (m, 2H), 5.42-5.64 (m, 2H), 4.89 (s, 2H), 6.25 (1H), 7.00-7.49 (m, 12H), 7.68 (d, 1H, J=8 Hz); MS m/z 464 (MH$^+$)

Synthesis Example 7

Compound #16

2-(dimethylamino)-1-(6-phenethyl-7-(trifluoromethyl)-3,4-dihydro-[1,4]diazepino[6,7,1-hi]indol-2(1H)-yl)ethanone

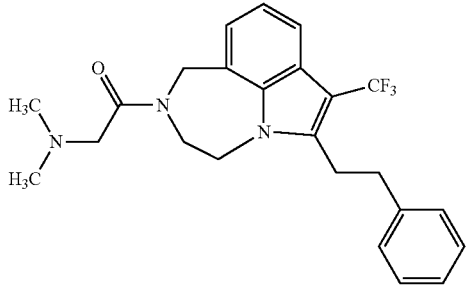

To 6-phenethyl-7-(trifluoromethyl)-1,2,3,4-tetrahydro-[1,4]diazepino[6,7,1-hi]indole (prepared as described in Example 2 above, 37 mg, 0.1 mmol) and N,N-dimethylglycine hydrochloride (14 mg, 0.1 mmol) in THF (7 mL) was added triethylamine (50 mg, 0.5 mmol), and 2-(7-aza-1H-benzotriazole-1-yl)-1,1,3,3-tetramethyluronium hexafluorophosphate (HATU; 43 mg, 0.1 mmol). The resulting mixture was stirred overnight, then partitioned between ethyl acetate and water. The organic phase was washed sequentially with NaHCO$_3$ and brine, then dried and concentrated. The residue was purified by reverse-phase chromatography (acetonitrile/water/trifluoroacetic add) to yield 2-(dimethylamino)-1-(6-phenethyl-7-(trifluoromethyl)-3,4-dihydro-[1,4]diazepino[6,7,1-hi]indol-2(1H)-yl)ethanone.

$^1$H NMR (400 MHz, CD$_3$OD) δ 277 (⅔ of s, 6H), 2.80 (⅓ of s, 6H), 2.80-2.89 (m, 2H), 3.13-3.22 (overlapping m, 4H), 4.82 (s, 2H), 7.02-7.22 (m, 7H), 7.22-7.48 (m, 1H); MS m/z 430 (MH$^+$)

Synthesis Example 8

Compound #17

6-phenethyl-7-(trifluoromethyl)-3,4-dihydro-[1,4]diazepino[6,7,1-hi]indole-2(1H)-carboximidamide

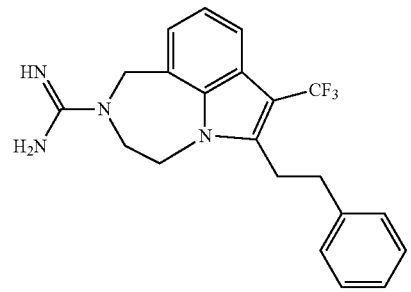 [SMILES: N=C(N)N1CCn2c(CCc3ccccc3)c(C(F)(F)F)c3cccc(c32)C1]

Mercuric chloride (41 mg, 0.15 mmol) was added to a mixture of 6-phenethyl-7-(trifluoromethyl)-1,2,3,4-tetrahydro-[1,4]diazepino[6,7,1-hi]indole (prepared as described in Example 2 above, 53 mg, 0.14 mmol), bis-N-Boc thiourea (38 mg, 0.14 mmol) and triethylamine (0.45 mmol) in DMF (5 mL) at 0° C. After 1 h of stirring at 0° C., ethyl acetate was added. The resulting mixture filtered and the filtrate washed sequentially with water and brine then dried (Na$_2$SO$_4$) and concentrated. The resulting residue was purified by reverse-phase chromatography to yield Z-tert-butyl(((tert-butoxycarbonyl)imino)(6-phenethyl-7-(trifluoromethyl)-3,4-dihydro-[1,4]diazepino[6,7,1-hi]indol-2(1H)-yl)methyl)carbamate (74 mg, MS m/z=587 (MH$^+$).

A solution of Z-tert-butyl(((tert-butoxycarbonyl)imino)(6-phenethyl-7-(trifluoromethyl)-3,4-dihydro-[1,4]diazepino[6,7,1-hi]indol-2(1H)-yl)methyl)carbamate (74 mg, 0.13 mmol) in CH$_2$Cl$_2$ (5 mL) was treated with 4M HCl in 1,4-dioxane (12 mL) and the resulting mixture was stirred at room temperature overnight. Evaporation of the solvent and trituration with diethyl ether yielded 6-phenethyl-7-(trifluoromethyl)-3,4-dihydro-[1,4]diazepino[6,7,1-hi]indole-2(1H)-carboximidamide (26 mg).

$^1$H NMR (400 MHz, CD$_3$OD) δ 2.97-3.00 (m, 2H), 3.22-3.33 (m, 2H), 3.82-3.85 (m, 2H), 4.38-4.41 (m, 2H), 4.89-5.00 (m, 2H), 7.13-7.31 (m, 7H), 7.60-7.62 (m, 1H); MS m/z 387 (MH+)

Synthesis Example 9

Compound #18

2-amino-1-(6-phenethyl-7-(trifluoromethyl)-3,4-dihydro-[1,4]diazepino[6,7,1-hi]indol-2(1H)-yl)ethanone

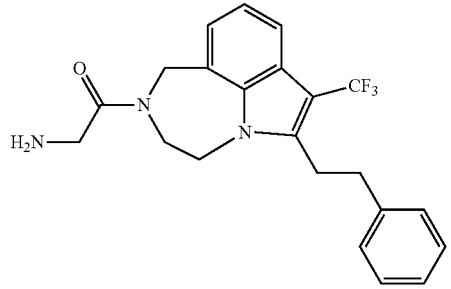

HATU (172 mg, 0.45 mmol) and triethylamine (1.97 mmol) was added to a mixture of 6-phenethyl-7-(trifluoromethyl)-1,2,3,4-tetrahydro-[1,4]diazepino[6,7,1-hi]indole (prepared as described in Example 2 above, 150 mg, 0.39 mmol) and N-Boc-glycine hydrochloride (72 mg, 0.41 mmol) in THF (7 mL). After stirring overnight, the resulting mixture was partitioned between ethyl acetate and water. The organic phase was washed sequentially with $NaHCO_3$ (sat'd., aq) and brine, then dried and concentrated. The resulting residue was purified by reverse-phase chromatography to yield tert-butyl (2-oxo-2-(6-phenethyl-7-(trifluoromethyl)-3,4-dihydro-[1,4]diazepino[6,7,1-hi]indol-2(1H)-yl)ethyl)carbamate (200 mg, MS m/z 502 (MH⁺).

To a solution of (2-oxo-2-(6-phenethyl-7-(trifluoromethyl)-3,4-dihydro-[1,4]diazepino[6,7,1-hi]indol-2(1-yl)ethyl)carbamate (200 mg, 0.40 mmol) in dichloromethane at 0° C. was added 4M HCl in 1,4-dioxane (0.5 mL). The resulting solution was stirred at room temperature overnight, and the resulting solids collected by filtration. Purification of the solid by reverse-phase chromatography yielded 2-amino-1-(6-phenethyl-7-(trifluoromethyl)-3,4-dihydro-[1,4]diazepino[6,7,1-hi]indol-2(1H)-yl)ethanone (127 mg).

MS m/z 402 (MH⁺)

Synthesis Example 10

Compound #20

2-oxo-2-(6-phenethyl-7-(trifluoromethyl)-3,4-dihydro-[1,4]diazepino[6,7,1-hi]indol-2(1H)-yl)ethyl acetate

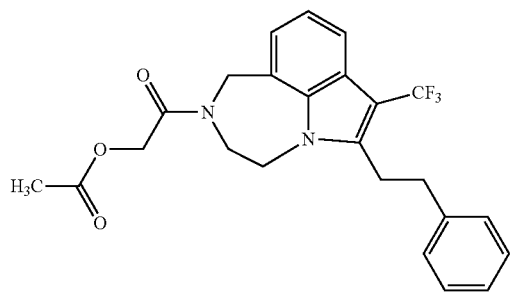 [SMILES: CC(=O)OCC(=O)N1CCn2c(CCc3ccccc3)c(C(F)(F)F)c3cccc(c32)C1]

To a solution of 6-phenethyl-7-(trifluoromethyl)-1,2,3,4-tetrahydro-[1,4]diazepino[6,7,1-hi]indole (prepared as described in Example 2 above, 53 mg, 0.14 mmol) in $CH_2Cl_2$ at 0° C. was added 2-acetoxyacetyl chloride (19 mg, 0.14 mmol) and diisopropylethylamine (0.072 mL, 0.42 mmol) and the resulting mixture stirred at 0° C. Upon completion of the reaction completion, the solvent was evaporated and the resulting residue triturated with methanol-diethyl ether to yield 2-oxo-2-(6-phenethyl-7-(trifluoromethyl)-3,4-dihydro-[1,4]diazepino[6,7,1-hi]indol-2(1H)-yl)ethyl acetate (20 mg) as a white solid.

¹H NMR (400 MHz, CDCl₃) δ 2.11 (⅘ of s, 3H), 2.11 (⅘ of s, 3H), 2.17 (⅕ of s, 3H), 2.93-2.99 (m, 2H), 3.16-3.22 (m, 2H), 3.43-3.44 (¼ of m, 2H), 3.45-3.50 (¼ of m, 2H), 3.92-4.08 (¾ of m, 2H), 4.11-4.13 (2H, m), 4.55 (⅛ of s, 4H,), 4.80, (¾ of s, 4H), 5.03 (s, ⅛ of s, 4H), 7.11-7.70 (m, 8H)

Synthesis Example 11

Compound #21

3,3,3-trifluoro-1-(6-phenethyl-7-(trifluoromethyl)-3,4-dihydro-[1,4]diazepino[6,7,1-hi]indol-2(1H)-yl)propan-1-one A mixture of 6-phenethyl-7-(trifluoromethyl)-1,2,3,4-tetrahydro-[1,4]diazepino[6,7,1-hi]indole (prepared as described in Example 2 above, 66 mg, 0.17 mmol), 3-trifluoromethylpropionic acid (23 mg, 0.18 mmol), HATU (75 mg, 0.2 mmol) and triethylamine (87 mg, 0.86 mmol) in THF (7 mL) was stirred overnight. The resulting mixture was partitioned between etyl acetate and water, and the organic layer was washed sequentially with $NaHCO_3$ (sat'd) and brine, then dried ($Na_2SO_4$) and concentrated. The residue was purified by reverse-phase chromatography ($CH_3CN/H_2O$-TFA) to yield 3,3,3-trifluoro-1-(6-phenethyl-7-(trifluoromethyl)-3,4-dihydro-[1,4]diazepino[6,7,1-hi]indol-2(1H)-yl)propan-1-one.

¹H NMR (400 MHz, CDCl₃) δ 2.92-3.31 (overlapping m, 6H), 3.92-4.07 (m, 2H), 4.09-4.12 (m, 2H), 4.84 (s, 2H), 7.00-7.71 (m, 8H); MS m/z 455 (MH⁺)

Synthesis Example 12

Compound #22

4,4,4-trifluoro-3-methyl-1-(6-phenethyl-7-(trifluoromethyl)-3,4-dihydro-[1,4]diazepino[6,7,1-hi]indol-2(1H)-yl)butan-1-one

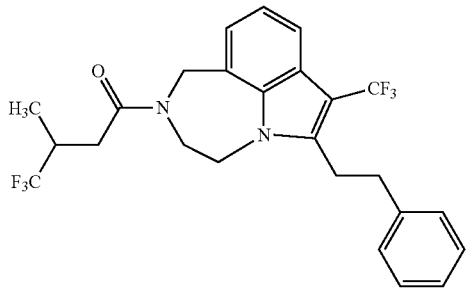 [SMILES: CC(CC(=O)N1CCn2c(CCc3ccccc3)c(C(F)(F)F)c3cccc(c32)C1)C(F)(F)F]

A mixture of 6-phenethyl-7-(trifluoromethyl)-1,2,3,4-tetrahydro-[1,4]diazepino[6,7,1-hi]indole (prepared as described in Example 2 above, 64 mg, 0.17 mmol), 3-(trifluoromethyl)butanoic acid (27 mg, 0.18 mmol), HATU (73 mg, 0.2 mmol) and triethylamine (85 mg, 0.84 mmol) in THF (7 mL) was stirred overnight. The resulting mixture was partitioned between ethyl acetate and water, and the organic layer was washed sequentially with NaHCO$_3$ (sat'd) and brine, then dried and concentrated. The residue was purified by reverse-phase chromatography (CH$_3$CN-water/TFA) to yield 4,4,4-trifluoro-3-methyl-1-(6-phenethyl-7-(trifluoromethyl)-3,4-dihydro-[1,4]diazepino[6,7,1-hi]indol-2(1H)-yl)butan-1-one (78 mg).

$^1$H NMR (CDCl$_3$) δ 1.04 (⅔ of a t, 3H, J=7 Hz), 1.20 (⅓ of a t, 3H, J=7 Hz), 2.02-3.54 (overlapping m, 6H), 3.81-4.24 (overlapping m, 2H), 4.82-4.98 (m, 2H), 7.01-7.37 (m, 7H), 7.62-7.71 (m, 1H); MS m/z 482 (MH$^+$)

Synthesis Example 13

Compound #23

2-(6-phenethyl-7-(trifluoromethyl)-3,4-dihydro-[1,4]diazepino[6,7,1-hi]indol-2(1H)-yl)ethanol

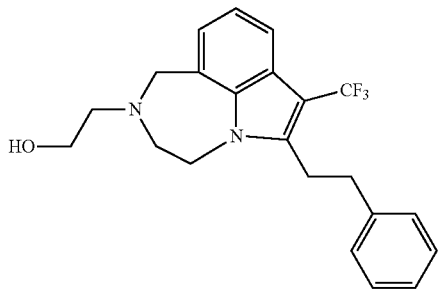 [SMILES: OCCN1CCn2c(CCc3ccccc3)c(C(F)(F)F)c3cccc(c32)C1]

A mixture of 6-phenethyl-7-(trifluoromethyl)-1,2,3,4-tetrahydro-[1,4]diazepino[6,7,1-hi]indole (prepared as described in Example 2 above, 100 mg, 0.26 mmol), 2-bromoethoxy t-butyl(dimethyl)silane (63 mg, 0.26 mmol) and diisopropylethylamine (0.09 mL, 0.53 mmol) in THF was heated at 80° C. for 5 h. The solvent was evaporated to yield 2-(2-(((tert-butyldimethylsilyl)oxy)ethyl-6-phenethyl-7-(trifluoromethyl)-1,2,3,4-tetrahydro-[1,4]diazepino[6,7,1-hi]indole (107 mg, MS m/z 503 (MH$^+$)).

To a mixture of 2-(2-(((tert-butyldimethylsilyl)oxy)ethyl-6-phenethyl-7-(trifluoromethyl)-1,2,3,4-tetrahydro-[1,4]diazepino[6,7,1-hi]indole (107 mg, 0.21 mmol) in THF was added conc. HCl (2 mL) at 0° C. and the resulting mixture stirred for 1 h. Purification by reverse-phase chromatography (25→90% CH$_3$CN—H$_2$O-TFA) yielded 2-(6-phenethyl-7-(trifluoromethyl)-3,4-dihydro-[1,4]diazepino[6,7,1-hi]indol-2(1H)-yl)ethanol (50 mg).

$^1$H NMR (400 MHz, CD$_4$OD) δ 2.96-3.00 (m, 2H), 3.24-3.65 (overlapping m, 4H), 3.87-4.00 (m, 2H), 4.40-4.41 (overlapping m, 4H), 7.12-7.32 (m, 7H), 7.68-7.70 (m, 1H); MS m/z 389 (MH$^+$)

Synthesis Example 14

Compound #24

2-(methylsulfonyl)-6-phenethyl-7-(trifluoromethyl)-1,2,3,4-tetrahydro-[1,4]diazepino[6,7,1-hi]indole

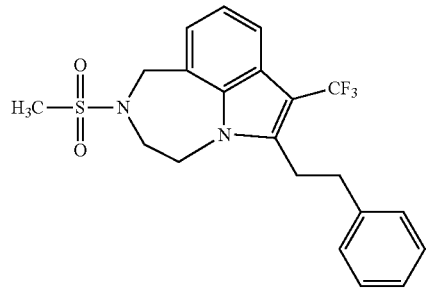 [SMILES: CS(=O)(=O)N1CCn2c(CCc3ccccc3)c(C(F)(F)F)c3cccc(c32)C1]

A solution of 6-phenethyl-7-(trifluoromethyl)-1,2,3,4-tetrahydro-[1,4]diazepino[6,7,1-hi]indole (prepared as described in Example 2 above, 53 mg, 0.14 mmol), methanesulfonyl chloride (16 mg, 0.14 mmol) and diisopropylethylamine (0.072 mL, 0.42 mmol) in CH$_2$Cl$_2$ (3 mL) was stirred overnight. The solvent was evaporated under reduced pressure and the resulting residue purified by trituration from methanol-diethyl ether to 2-(methylsulfonyl)-6-phenethyl-7-(trifluoromethyl)-1,2,3,4-tetrahydro-[1,4]diazepino[6,7,1-hi]indole (43 mg).

$^1$H NMR (400 MHz, CDCl$_3$) δ 2.35 (s, 3H), 2.96-3.00 (m, 2H), 3.19-3.23 (m, 2H), 3.55-3.57 (m, 2H), 4.08-4.11 (m, 2H), 4.85 (s, 2H), 7.00-7.32 (m, 8H), 7.64-7.66 (m, 1H); MS m/z 423 (MH$^+$)

Synthesis Example 15

Compound #25

5-phenethyl-6-(trifluoromethyl)-2,3-dihydro-[1,4]oxazino[2,3,4-hi]indole

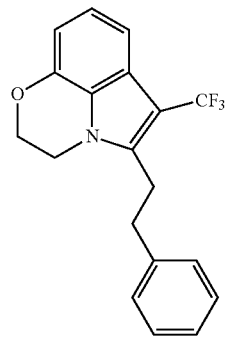 [SMILES: FC(F)(F)c1c(CCc2ccccc2)n2c3c(cccc13)OCC2]

A solution of 2-ethoxy-3-phenethyl-2-(trifluoromethyl) oxirane (340 mg, 1.3 mmol) and 3,4-dihydro-2H-benzo[b][1,4]oxazine (177 mg, 1.3 mmol) in hexafluoroisopropanol was stirred at room temperature overnight. The solvent was evaporated and the residue purified by reverse-phase HPLC (CH₃CN/0.1% trifluoroacetic acid) to yield 5-phenethyl-6-(trifluoromethyl)-2,3,5,6-tetrahydro-[1,4]oxazino[2,3,4-hi]indol-6-ol as a solid (MS m/z 350 MH+).

To a solution of 5-phenethyl-6-(trifluoromethyl)-2,3,5,6-tetrahydro-[1,4]oxazino[2,3,4-hi]indol-6-ol (208 mg, 0.60 mmol) in pyridine (3 mL) was added thionyl chloride (142 mg, 1.2 mmol) at 0° C. After stirring for 2 h at 0° C., the resulting mixture was concentrated to yield 5-phenethyl-6-(trifluoromethyl)-2,3-dihydro-[1,4]oxazino[2,3,4-hi]indole.

$^1$H NMR (400 MHz, CDCl₃) δ 2.98-3.23 (m, 4H), 3.31-3.72 (m, 2H), 4.15 (m, 2H), 6.65-7.22 (m, 8H); MS m/z 332 (MH⁺)

Compounds 26-28 were similarly prepared according to the procedure as described in Example 15 above, selecting and reacting a suitably selected oxirane (2-ethoxy-3-phenethyl-2-(trifluoromethyl)oxirane or 2-ethoxy-3-(3-phenoxypropyl)-2-(trifluoromethyl)oxirane) with a suitably selected, commercially available amine.

| Compound No. | Measured MH⁺ |
|---|---|
| 26 | 346 |
| 27 | 362 |
| 28 | 362 |

Example 16

Reference Compound (#2)

2-Phenethyl-1-(trifluoromethyl)-5,6-dihydro-4H-pyrrolo[3,2,1-ij]quinoline

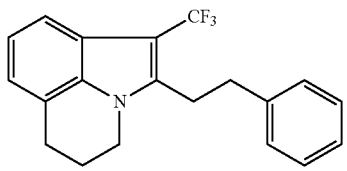 [SMILES: FC(F)(F)c1c(CCc2ccccc2)n2c3c(cccc13)CCC2]

2-Phenethyl-1-(trifluoromethyl)-5,6-dihydro-4H-pyrrolo[3,2,1-ij]quinoline (CA Registry number 866049-84-5, Registered 25 Oct. 2005) was purchased from Key Organics, Ltd. (Highfield Road Industrial Estate, Camelford, Cornwall, PL32 9RA, United Kingdom).

Biological Example 1

Endothelial Lipase Assay (Human/Mouse)

To assay for cell surface lipase activity, cells expressing human endothelial lipase (EL) or LPL were plated in CellBIND® 384-well plates (Corning, Lowell, Mass.) in 25 µL serum free medium at a density of 2000 cells/well. After 18-24 hours incubation at 37° C., the medium was removed and replaced with 15 µL assay buffer [Hank's Buffered Saline Solution with 25 mM HEPES pH 7.2] and 15 µL PLA₁ substrate for a final concentration of 10 µM using a Multidrop reagent dispenser. Fluorescence signal was monitored for 30 min at 37° C. on a Safire II plate reader in kinetic mode (60 cycles, kinetic interval: 30 seconds) with an excitation wavelength of 490 nm and an emission wavelength of 515 nm. Linear regression of the fluorescence intensity collected from 480 to 1500 seconds was used to calculate the reaction rate (the slope) and the slopes were used to calculate IC₅₀ values where appropriate. The amount of BODIPY-labeled product generated was calculated at the 30 min time point as determined from standard curve analysis of purified BODIPY FL C₅. In all studies using the inhibitor Ebelactone B, consistent results were obtained when it was dissolved as a stock in DMSO, immediately before use.

Representative compounds of the present invention (prepared as described in the schemes outlined herein) were tested according to the procedures as described above, with calculated IC₅₀ values (in µM) as listed in Table 5, below.

TABLE 5

| Mouse and Human EL IC₅₀ | | |
|---|---|---|
| Compound No. | Human IC₅₀ (µM) | Mouse IC₅₀ (µM) |
| 1 | 0.185 | 0.195 |
| 3 | 0.115 | 0.096 |
| 4 | 0.143 | 0.205 |
| 5 | 0.014 | 0.017 |
| 6 | 0.071 | 0.136 |
| 7 | 0.017 | 0.026 |
| 8 | 0.004 | 0.004 |
| 9 | 0.043 | 0.036 |
| 10 | 0.054 | 0.075 |
| 11 | 0.360 | 1.195 |
| 12 | 0.135 | 0.131 |
| 13 | 0.150 | 0.124 |
| 14 | 0.168 | 0.162 |
| 15 | 0.694 | 0.677 |
| 16 | 0.959 | 1.001 |
| 17 | 4.824 | 3.615 |
| 18 | 2.017 | 1.885 |
| 19 | 0.068 | 0.087 |
| 20 | 0.442 | 0.479 |
| 21 | 0.255 | 0.237 |
| 22 | 0.101 | 0.142 |
| 23 | 0.280 | 0.346 |
| 24 | 0.186 | 0.340 |
| 25 | 0.039 | 0.031 |
| 26 | 0.413 | 0.618 |
| 27 | 0.082 | 0.108 |
| 28 | 33.335 | 33.335 |
| Reference Compound | | |
| 2 | 0.022 | 0.048 |

Formulation Example 1

Prophetic Example

Solid Oral Dosage Pharmaceutical Composition

As a specific embodiment of an oral composition, 100 mg of a compound of formula (I) as herein described is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

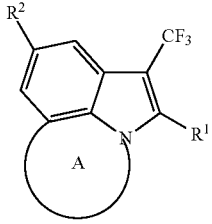
(I)

wherein

R¹ is selected from the group consisting of —(CH₂)ₐ-phenyl and —(CH₂)ᵦ—O-phenyl; wherein a is an integer from 1 to 5; b is an integer from 1 to 4; and wherein the phenyl portion of the R¹ group is optionally substituted with one to two substituents independently selected from the group consisting of halogen, $C_{1-4}$alkyl and $C_{1-4}$alkoxy;

R² is selected from the group consisting of hydrogen, hydroxy, methoxy and amino;

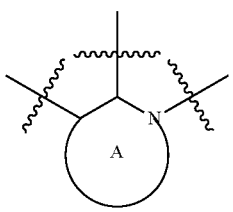

represents a five to seven membered, saturated ring structure selected from the group consisting of

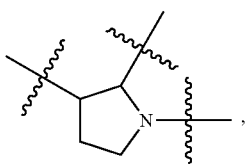
(a)

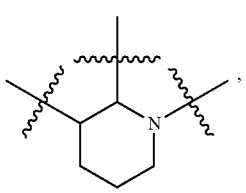
(b)

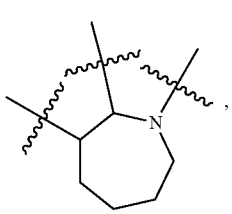
(c)

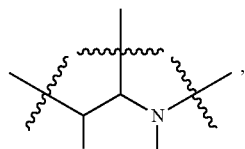
(d)

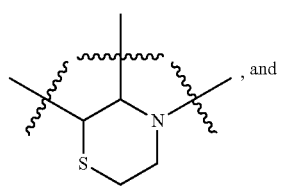
(e)
, and

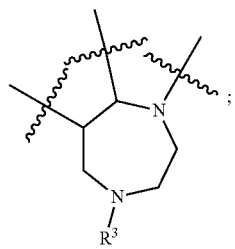
(f)

wherein R³ is selected from the group consisting of hydrogen, —$C_{1-4}$alkyl, —($C_{1-4}$alkyl)-OH, —C(O)—($C_{1-4}$alkyl), —C(O)—($C_{1-3}$alkyl)-CF₃, —C(O)O—($C_{1-4}$alkyl), —C(O)—CH₂—O—C(O)—($C_{1-4}$alkyl), —C(O)—NR^A R^B, —C(O)—NH-phenyl, —C(O)—CH₂—NR^A R^B, —C(=NH)—NR^A R^B, —SO₂—($C_{1-4}$alkyl) and —SO₂—NR^A R^B; and wherein R^A and R^B are each independently selected from the group consisting of hydrogen and $C_{1-4}$alkyl;

provided that when R¹ is —CH₂CH₂-phenyl and R² is hydrogen, then

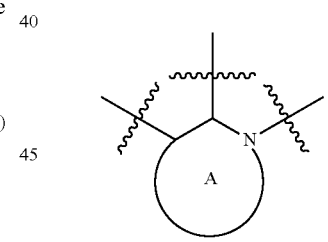

is other than

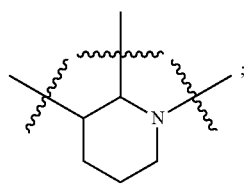 [SMILES: *C1CCCN(*)C1*]

or a pharmaceutically acceptable salt thereof.

2. A compound as in claim 1, wherein

R¹ is selected from the group consisting of —($C_{1-4}$alkyl)-phenyl and —($C_{1-3}$alkyl)-O-phenyl; wherein the phenyl portion of R¹ is optionally substituted with one to two substituents independently selected from the group consisting of halogen, $C_{1-2}$alkyl and $C_{1-2}$alkoxy;

R² is selected from the group consisting of hydrogen, hydroxy, methoxy and amino;

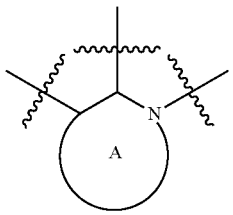

represents a five to seven membered, saturated ring structure selected from the group consisting of (a)
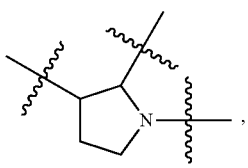

(b)
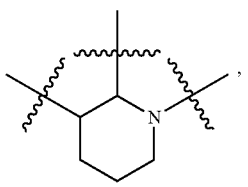 [SMILES: *C1CCCN(*)C1*]

(c)
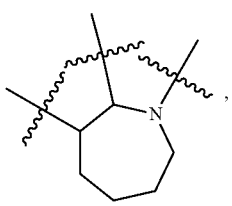

(d)
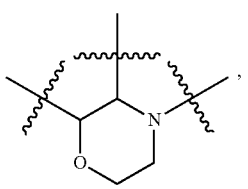

(e)
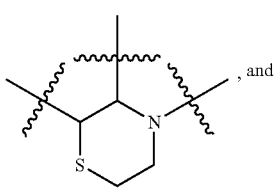, and (f)
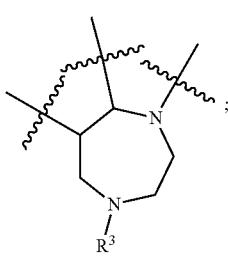;

wherein R³ is selected from the group consisting of hydrogen, —($C_{1-2}$alkyl), —($C_{1-4}$alkyl)-OH, —C(O)—($C_{1-2}$ alkyl), —C(O)—($C_{1-3}$alkyl)-CF₃, —C(O)O—($C_{1-4}$al-kyl), —C(O)—CH₂—O—C(O)—($C_{1-4}$alkyl), —C(O)—NR$^A$R$^B$, —C(O)—NH-phenyl, —C(O)—CH₂—NR$^A$R$^B$, —C(=NH)—NH₂, —SO₂—($C_{1-4}$ alkyl) and —SO₂—NR$^A$R$^B$; and wherein R$^A$ and R$^B$ are each independently selected from the group consisting of hydrogen and $C_{1-4}$alkyl;

provided that when R¹ is —CH₂CH₂-phenyl and R² is hydrogen, then

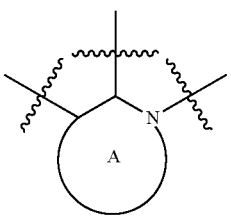

is other than

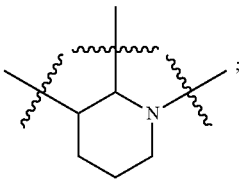;

or a pharmaceutically acceptable salt thereof.

3. A compound as in claim 2, wherein

R¹ is selected from the group consisting of —($C_{1-3}$alkyl)-phenyl and —($C_3$alkyl)-O-phenyl;

R² is selected from the group consisting of hydrogen, hydroxy, methoxy and amino;

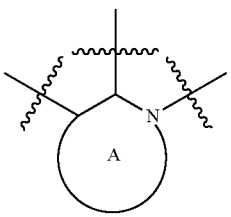

represents a five to seven membered, saturated ring structure selected from the group consisting of (a)
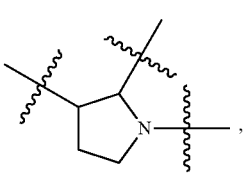

-continued (b)
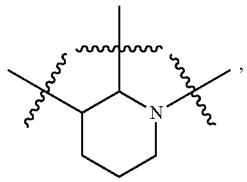, (c)
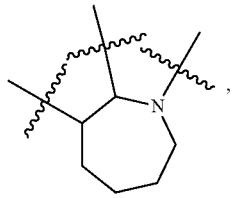, (d)
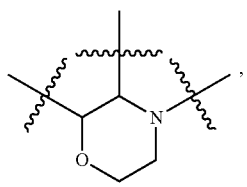, (e)
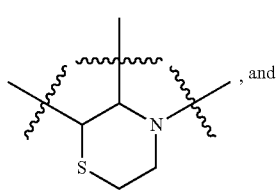, and (f)
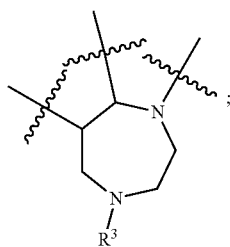;

wherein R³ is selected from the group consisting of hydrogen, —(C$_{1-2}$alkyl)-OH, —C(O)—(C$_{1-3}$alkyl)-CF$_3$, —C(O)O—(C$_{1-4}$alkyl), —C(O)—CH$_2$—O—C(O)—(C$_{1-2}$alkyl), —C(O)—NHR$^A$, —C(O)—NH-phenyl, —C(O)—CH$_2$—NR$^A$R$^B$, —C(=NH)—NH$_2$, —SO$_2$—(C$_{1-2}$alkyl) and —SO$_2$—NH$_2$; and wherein R$^A$ and R$^B$ are each independently selected from the group consisting of hydrogen and C$_{1-4}$alkyl;

provided that when R¹ is —CH$_2$CH$_2$-phenyl and R² is hydrogen, then

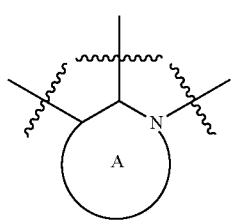

is other than

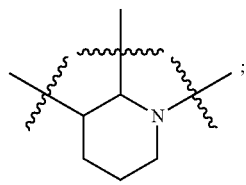 [SMILES: *C1CCCN(*)C1*];

or a pharmaceutically acceptable salt thereof.

4. A compound as in claim 3, wherein

R¹ is selected from the group consisting of —CH$_2$-phenyl, —CH$_2$CH$_2$-phenyl, —CH$_2$CH$_2$CH$_2$-phenyl and —CH$_2$CH$_2$CH$_2$—O-phenyl;

R² is selected from the group consisting of hydrogen, hydroxy, methoxy and amino;

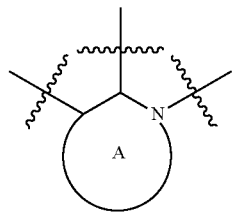

represents a five to seven membered, saturated ring structure selected from the group consisting of (a)
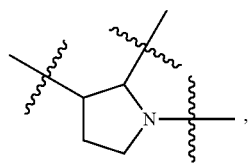, (b)
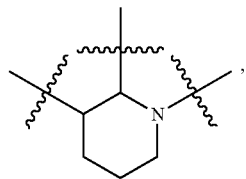 [SMILES: *C1CCCN(*)C1*], (c)
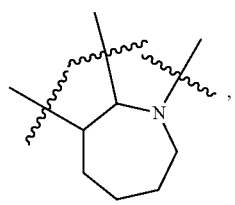, (d)
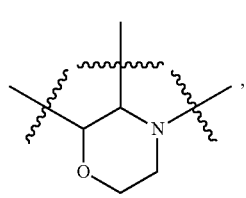,

47 / 48

-continued (e)
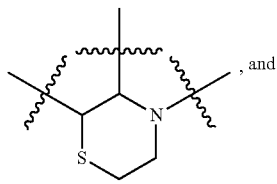
, and (f)
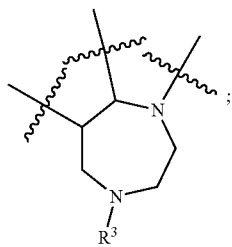
;

wherein R³ is selected from the group consisting of hydrogen, —CH₂CH₂—OH, —C(O)—O—C(CH₃)₃, —C(O)—CH₂—CF₃, —C(O)—CH₂—CH(CH₃)—CF₃, —C(O)—CH₂—O—C(O)—CH₃, —C(O)—NH—CH(CH₃)₂, —C(O)—NH-phenyl, —C(O)—CH₂—NH₂, —C(O)—CH₂—N(CH₃)₂, —C(=N)—NH₂, —SO₂—CH₃ and —SO₂—NH₂;

provided that when R¹ is —CH₂CH₂-phenyl and R² is hydrogen, then

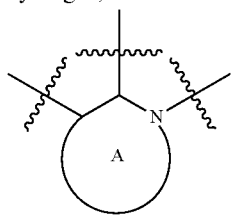

is other than

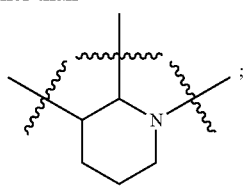
;

or a pharmaceutically acceptable salt thereof.

5. A compound as in claim 4, wherein
R¹ is selected from the group consisting of —CH₂-phenyl, —CH₂CH₂-phenyl, —CH₂CH₂CH₂-phenyl and —CH₂CH₂CH₂—O-phenyl;
R² is selected from the group consisting of hydrogen, hydroxy, methoxy and amino;

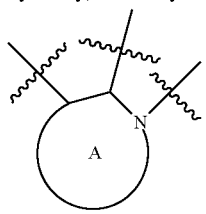

represents a five to seven membered, saturated ring structure selected from the group consisting of (a)
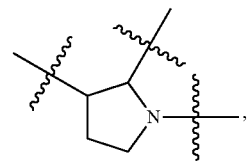
, (b)
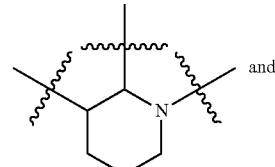
and (c)
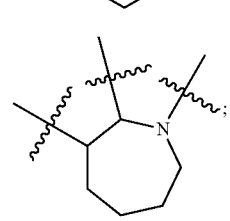
;

provided that when R¹ is —CH₂CH₂-phenyl and R² is hydrogen, then

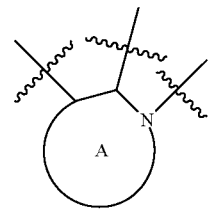

is other than

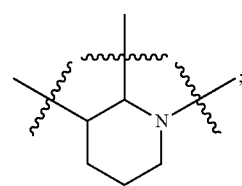
;

or a pharmaceutically acceptable salt thereof.

6. A compound as in claim 5, wherein
R¹ is selected from the group consisting of —CH₂-phenyl, —CH₂CH₂-phenyl and —CH₂CH₂CH₂—O-phenyl;
R² is selected from the group consisting of hydrogen, hydroxy, methoxy and amino;

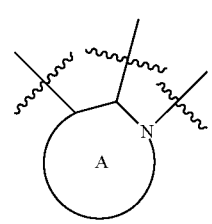

represents a five to seven membered, saturated ring structure selected from the group consisting of

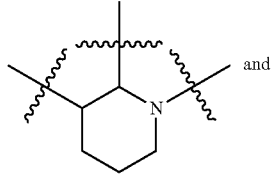 and (b)

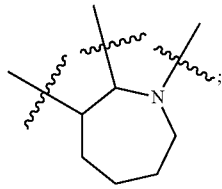 ; (c)

provided that when R¹ is —CH₂CH₂-phenyl and R² is hydrogen, then

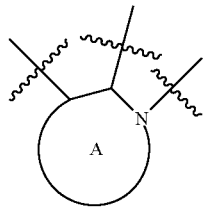

is other than

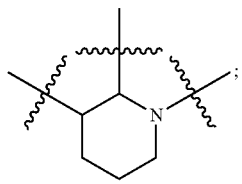 [SMILES: *C1CCCN(*)C1*] ;

or a pharmaceutically acceptable salt thereof.

7. A compound as in claim 4, wherein
R¹ is —CH₂CH₂-phenyl;
R² is hydrogen;

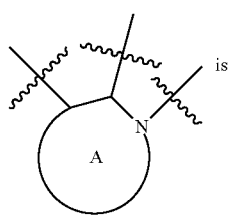 is

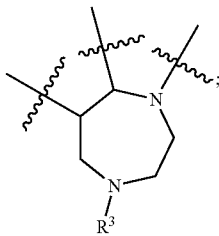 (f)

R³ is selected from the group consisting of hydrogen, —CH₂CH₂—OH, —C(O)—O—C(CH₃)₃, —C(O)—CH₂—CF₃, —C(O)—CH₂—CH(CH₃)—CF₃, —C(O)—CH₂—O—C(O)—CH₃, —C(O)—NH—CH(CH₃)₂, —C(O)—NH-phenyl, —C(O)—CH₂—NH₂, —C(O)—CH₂—N(CH₃)₂, —C(=N)—NH₂, —SO₂—CH₃ and —SO₂—NH₂;

or a pharmaceutically acceptable salt thereof.

8. A compound as in claim 7, wherein
R¹ is —CH₂CH₂-phenyl;
R² is hydrogen;

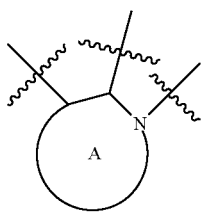

is

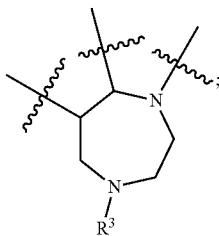 (f)

R³ is selected from the group consisting of —C(O)—O—C(CH₃)₃, —C(O)—CH₂—CH(CH₃)—CF₃, —C(O)—NH—CH(CH₃)₂, —C(O)—NH-phenyl, —SO₂—CH₃ and —SO₂—NH₂;

or a pharmaceutically acceptable salt thereof.

9. A compound as in claim 4, wherein
R¹ is selected from the group consisting of —CH₂CH₂-phenyl, —CH₂CH₂CH₂-phenyl and —CH₂CH₂CH₂—O-phenyl;

$R^2$ is hydrogen:

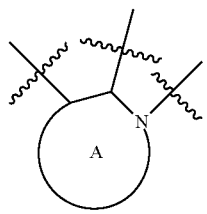

is

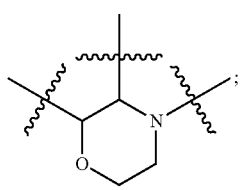 [SMILES: *C1CCCN(*)C1*]

(d)

or a pharmaceutically acceptable salt thereof.

10. A compound as in claim 1 selected from the group consisting of:

| Compound No. | A | $R^1$ | $R^2$ |
|---|---|---|---|
| 1 | pyrrolidine | —(CH₂CH₂CH₂)-phenyl | H |
| 3 | piperidine | —(CH₂)-phenyl | H |
| 4 | piperidine | —(CH₂CH₂CH₂)-phenyl | H |
| 5 | piperidine | —(CH₂CH₂)-phenyl | —OCH₃ |
| 6 | piperidine | —(CH₂CH₂)-phenyl | —OH |
| 8 | piperidine | —(CH₂CH₂CH₂)—O—phenyl | —NH₂ |
| 9 | azepane | —(CH₂CH₂)-phenyl | H |
| 10 | azepane | —(CH₂)-phenyl | H |
| 11 | azepane | —(CH₂CH₂CH₂)-phenyl | H | and pharmaceutically acceptable salts thereof.

11. A compound as in claim 1 wherein $R^1$ is —CH₂CH₂-phenyl; $R^2$ is hydrogen;

is

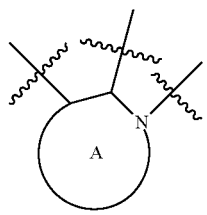

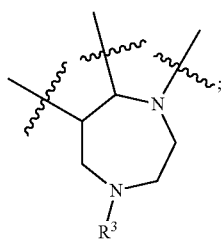

and R³ is selected from the group consisting of:

| Compound No. | R³ |
| --- | --- |
| 12 | —C(O)—NH—CH(CH₃)₂ |
| 13 | —C(O)—O—C(CH₃)₃ |
| 14 | —C(O)—NH-phenyl |
| 15 | H |
| 16 | —C(O)—CH₂—N(CH₃)₂ |
| 17 | —C(=N)—NH₂ |
| 18 | —C(O)—CH₂—NH₂ |
| 19 | —SO₂—NH₂ |
| 20 | —C(O)—CH₂—O—C(O)—CH₃ |
| 21 | —C(O)—CH₂—CF₃ |
| 22 | —C(O)—CH₂—CH(CH₃)—CF₃ |
| 23 | —CH₂CH₂—OH |
| 24 | —SO₂—CH₃ | or a pharmaceutically acceptable salt thereof.

12. A compound as in claim 1 selected from the group consisting of:

| Compound No. | A | R¹ | R² |
| --- | --- | --- | --- |
| 25 | (morpholine structure) | —(CH₂CH₂)-phenyl | H |
| 26 | (morpholine structure) | —(CH₂CH₂CH₂)-phenyl | H |
| 27 | (morpholine structure) | —(CH₂CH₂CH₂)—O-phenyl | H | and pharmaceutically acceptable salts thereof.

13. A pharmaceutical composition comprising a pharmaceutically acceptable carrier and a compound of claim 1.

14. A process for making a pharmaceutical composition comprising mixing a compound of claim 1 and a pharmaceutically acceptable carrier.

15. A method of treating a disorder selected from the group consisting of atherosclerosis, dyslipidemia, low HDL, and high LDL in subject in need thereof, comprising administering to said subject a therapeutically effective amount of the composition of claim 13.

16. A method of treating a disorder selected from the group consisting of atherosclerosis, dyslipidemia, low HDL, and high LDL in subject in need thereof, comprising administering to said subject a therapeutically effective amount of the compound of claim 1.

* * * * *